United States Patent [19]

Parker

[11] Patent Number: 5,091,545
[45] Date of Patent: Feb. 25, 1992

[54] CATALYTIC OXIDATION OF HYDROXY CONTAINING AROMATIC COMPOUNDS

[75] Inventor: Dane K. Parker, Massillon, Ohio

[73] Assignee: The Goodyear Tire & Rubber Company, Akron, Ohio

[21] Appl. No.: 487,361

[22] Filed: Mar. 2, 1990

[51] Int. Cl.$^5$ ............... C07C 249/02; C07C 251/22
[52] U.S. Cl. ................... 552/302; 552/307; 552/309
[58] Field of Search ............ 552/302, 307, 309

[56] References Cited

U.S. PATENT DOCUMENTS

| | | | |
|---|---|---|---|
| 2,170,191 | 8/1939 | Fisher | 18/53 |
| 3,663,578 | 5/1972 | Von Kutepow | 552/309 |
| 3,966,776 | 6/1976 | Kato et al. | 552/309 |

OTHER PUBLICATIONS

Nishinaga, A., et al, Chemistry Lett. (1985) 1319-22.
Nishinaga, A., et al, Chemistry Lett. (1985) 905-908.
Nishinaga, A., et al, Chemistry Lett. (1983) 1751-54.
Nishinaga, A., et al, Chemistry Lett. (1986) 505-506.
Nishinaga, A., et al, Bull. Chemical Soc. of Japan 48(5) (1975), 1683.
Nishinaga, A., et al, J. Chem. Soc., Dalton Trans. (7) (1981), 1504-14.
Billing, I. R., et al, Plastics & Rubber:Processing, Sep. (1977), 83-86.
Numata, T., et al, Tetrahedron Lett. 49 (1978), 4933-36.
Collins, T. J., et al, J. Chem. Soc., Chem. Commun. (1987), 803-04.
Felthouse, T. R., J. Am. Chem. Soc. 109 (1987), 7566-68.
McKillop, et al, Synthesis, Dec. (1977) 847-48.
Cain, M. E. et al, Rubber Industry 9 (1975) 216-226.
Cunningham, D., et al, J. Chem. Soc. Chem. Commun. (1985), 231.
Matsuura, A., Chem. Lett. (1985), 993-96.
Inoki, S., et al, Chem. Lett. (1989), 515-518.
Mukaiyama, T., et al, Chem. Lett. (1989), 449-52.
Yamada, T. et al, Chem. Lett. (1989), 519-22.
Ganeshpure, P. A., et al, Tetrahedron Letters, vol. 30, No. 43 (1989), 5929-32.
Sakata, K. et al, Inorganica Chemica Acta, 144 (1985), 1-3.
Takehira, K., et al, J. Chem. Soc., Chem. Commun. (1989) 1705-6.
Nishinaga, A., et al, Tetrahedron Lett. 21 (1980), 4849-52.
Nishinaga, A., et al, J. of Mol. Catalysis, 48 (1988), 249-264.
Nishinaga, A. et al, Tetrahedron Lett., 21 (1980) 1261-64.
Nishinaga, A., et al, Tetrahedron Lett., 29 (1988) 4115-18.
Nishinaga, A., et al, Tetrahedron Lett., 31 (1979) 2893-96.
Nishinaga, A., et al, Tetrahedron Lett., 27 (1986) 2649-52.
Nishinaga, A., et al, Tetrahedron lett., 21 (1980) 1269-72.
Nishinaga, A., et al, Tetrahedron Lett., 22 (1981) 5293-96.
Nishinaga, A., et al, Tetrahedron Lett., 25 (1984) 5805-08.
Nishinaga, A., et al, Tetrahedron Lett., 21 (1980) 1265-68.
Nishinaga, A., et al, Tetrahedron Lett., 26 (50) (1987) 6309-12.

*Primary Examiner*—Vivian Garner
*Attorney, Agent, or Firm*—Bruce J. Hendricks

[57] ABSTRACT

The present invention relates to a process for the catalytic oxidation of hydroxy containing aromatic compounds to form the respective quinone compounds comprising contacting a hydroxy containing aromatic compound of the formula:

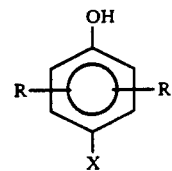

with a molecular oxygen containing gas in the presence of:
(a) a catalytic amount of a cobalt (II) compound,
(b) a primary aliphatic amine having the nitrogen atom attached to a tertiary carbon, and
(c) an alcohol selected from the group consisting of methyl alcohol, ethyl alcohol, isopropyl alcohol, butyl alcohol, 2,2,2-trifluoroethanol and benzyl alcohol,
wherein X is of the formula

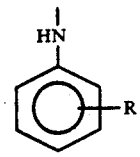

wherein R is individually selected from the group of radicals consisting of hydrogen, an alkyl having from about 1 to about 18 carbon atoms, an alkoxy having from about 1 to 8 carbon atoms, a phenyl and an aralkyl having 7 to 12 carbon atoms.

7 Claims, No Drawings

CATALYTIC OXIDATION OF HYDROXY CONTAINING AROMATIC COMPOUNDS

BACKGROUND OF THE INVENTION

The present invention relates to a process for the catalytic oxidation of hydroxy containing aromatic compounds to form their respective quinone compounds. Representative of the type of quinone compounds which may be prepared according to the process of the present invention include N-phenylquinone amines which have a number of utilities including use as an antioxidant in rubbers.

Hydroxy containing aromatic compounds have been oxidized by a variety of methods known to those skilled in the art. In this regard, attention is directed to "Catalytic Oxidations of Hydroquinones and 1,2-Diphenylhydrazine in the Presence of (Dibenzo[b, i][1,4,8,11]tetraazacyclotetradecinato) cobalt (II)", K. Sakata et al, Inorganica Chimica, 144 (1988) p. 1-3.

SUMMARY OF THE INVENTION

The present invention relates to a process for the oxidation of hydroxy containing aromatic compounds by contacting the hydroxy containing compound with a molecular oxygen containing gas in the presence of:
(a) a catalytic amount of a cobalt (II) compound,
(b) a primary aliphatic amine having the nitrogen atom attached to a tertiary carbon, and
(c) an alcohol diluent/solvent.

DETAILED DESCRIPTION OF THE PREFERRED EMBODIMENT

There is disclosed a process for the catalytic oxidation of hydroxy containing aromatic compounds comprising contacting a hydroxy containing aromatic compound of the formula:

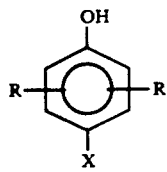

with a molecular oxygen containing gas in the presence of:
(a) a catalytic amount of a cobalt (II) compound,
(b) a primary aliphatic amine having the nitrogen atom attached to a tertiary carbon, and
(c) an alcohol selected from the group consisting of methyl alcohol, ethyl alcohol, isopropyl alcohol, butyl alcohol, 2,2,2-trifluoroethanol and benzyl alcohol,
wherein X is of the formula

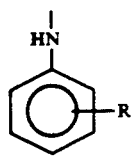

wherein R is individually selected from the group of radicals consisting of hydrogen, an alkyl having from about 1 to about 18 carbon atoms, an alkoxy having 1 to 8 carbon atoms, a phenyl and an aralkyl having 7 to 12 carbon atoms.

As disclosed above, the present invention may be used to oxidize a number of hydroxy containing aromatic compounds. Representative of such a compound is p-hydroxydiphenylamine.

A significant aspect of the present invention is conducting the oxidation reaction in the presence of a primary aliphatic amine having the nitrogen atom attached to a tertiary carbon. Representative of such primary aliphatic amines include those of the formula:

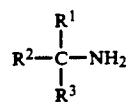

wherein $R^1$, $R^2$ and $R^3$ may be the same or different and are independently selected from the group of radicals consisting of an alkyl having 1 to 20 carbon atoms, or a hydroxy or alkoxy substituted alkyl having 1 to 16 carbon atoms; and so long as the total number of carbon atoms for $R^1$, $R^2$ and $R^3$ does not exceed 20. Preferably, $R^1$, $R^2$ and $R^3$ are each alkyls having 1 carbon atom or $R^1$ and $R^2$ are alkyls having 1 carbon atom and $R^3$ is an alkyl having 5 carbon atoms or $R^1$ and $R^2$ are each an alkyl having 1 carbon atom and $R^3$ is a hydroxy substituted alkyl having 1 carbon atom. Representative of the primary aliphatic amines include tertiary butylamine, tertiary octylamine and 2-amino-2-methyl-1-propanol.

The oxidation reaction is conducted in the presence of a catalytic amount of a cobalt (II) compound. Representative examples of cobalt (II) compounds employable in the process of the invention include cobalt (II) salts of carboxylic acids, carbonyls, sulfates, nitrates, halides, organometallic compounds of those metals and unsaturated N-macrocyclic cobalt complexes. More specifically, examples of cobalt (II) compounds include cobalt (II) naphthenate, cobalt (II) octoate, cobalt (II) laurate, cobalt (II) stearate, cobalt (II) linoleate, cobalt (II) acetylacetonate, cobalt (II) nitrate, cobalt (II) fluoride, cobalt (II) sulfate, cobalt (II) carbonyl, and cobalt (II) chloride. Preferably the cobalt compound is cobalt (II) chloride. The concentration of the catalyst system in the liquid phase, in general, may vary widely, depending upon the nature and amount of material to be oxidized. In general, however, the quantity catalyst employed in the oxidation step will vary from about 0.01 to about 1,000 ppm of metal (or mixed metal) and greater, preferably from about 1 to about 100 ppm, by weight, in the total mixture. The catalyst concentration is also dependent upon temperature and conversion desired.

The oxidation reaction of the process of the present invention is conveniently carried out by the rapid passage of molecular oxygen containing gas, such as air, through a suitable reactor, to which there has been charged the alcohol solvent, the catalytic amount of cobalt (II) compound and primary aliphatic amine as disclosed herein. The molecular oxygen containing gas is brought into intimate contact with the liquid phase, for example, by the use of high-speed stirrers, nozzles or the like in any conventional manner.

The rate of input of molecular oxygen containing gas will depend upon the temperature and pressure utilized during the oxygenation period, and heat removal limitations since these oxidations are generally exothermic.

Normally, there is provided at least an amount theoretically sufficient to convert the starting material to the corresponding oxidation product, and preferably, in excess of this amount. One may use a flow rate ranging from about 10 to 1000 liters per liter of solution per hour for most conversions. Any unreacted oxygen may be recycled to the reactor.

The oxidation process is conducted in an alcohol diluent/solvent. Examples of alcohols which may be used in the present invention include methyl alcohol, ethyl alcohol, isopropyl alcohol, butyl alcohol, 2,2,2-trifluoroethanol and benzyl alcohol. Preferably, methyl alcohol is used.

The oxidation time will vary depending upon the structure of the compound to be oxidized, reaction temperature, solvent, catalyst type and catalyst concentration. Generally, lower catalyst concentrations are employed when operating at higher temperatures. The temperature of the oxidation reaction of the process of the present invention may range from about 0° C. to about 150° C., preferably from about 20° C. to about 60° C. The oxidation reaction may be conducted at a variety of pressures. For example pressures from about 1 to about 100 atmospheres, preferably from about 1 to about 5 atmospheres may be employed in order to maintain the reaction in liquid phase.

The present invention is illustrated by the following examples which are intended to be limiting.

EXAMPLE 1

Preparation of N-phenylquinoneimine

A 500 ml cylindrical glass reactor equipped with an internal cooling coil, thermometer, magnetic stirring bar and a fritted glass gas inlet tube was charged with 17.6 grams of p-hydroxydiphenylamine (0.095 moles), 0.015 grams of anhydrous cobalt (II) chloride and 250 ml of methanol. The mixture was stirred with cooling at 9° C. until all reactants were dissolved. 3.66 grams (0.05 moles) of t-butylamine were then added and oxygen bubbled through the mixture. The solution immediately turned dark and crystallization of the product occurred after 9–10 minutes. The oxygen purge was continued for another 5 minutes before the reaction was quenched by pouring the reaction mixture into excess cold water. The deep orange-red microcrystalline product was then filtered off and dried. A yield of 14.5 grams (83% yield) was recovered. The product identity was verified by gas chromatographic analysis against a known standard.

EXAMPLE 2

Preparation of N-phenylquinoneimine

A 500 ml cylindrical glass reactor equipped with an internal cooling coil, thermometer, magnetic stirring bar and a fritted glass gas inlet tube was charged with 17.6 grams of p-hydroxydiphenylamine (0.095 moles), 0.015 grams of cobalt (II) chloride in 250 ml of methanol. The mixture was stirred with cooling (external cooling bath) at 9° C. until all reactants were dissolved. 38.85 grams of tertiary-octyl amine (0.30 moles) was then added and oxygen bubbled through the mixture. The solution immediately turns dark and crystallization of the product occurred after 9–10 minutes. Oxygen purge was continued for another 5 minutes. Gas chromatographic analysis at this point indicated almost complete conversion to the desired product.

EXAMPLE 3

Preparation of N-Phenylquinoneimine

The procedure of Example 2 was repeated with the exception that 2-amino-2-methyl-1-propanol (0.05 moles) was substituted for tertiary-octyl amine. Gas chromatographic analysis indicated almost complete conversion to the desired product.

What is claimed is:

1. A process for the catalytic oxidation of hydroxy containing aromatic compounds comprising contacting a hydroxy containing aromatic compound of the formula:

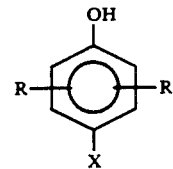

with a molecular oxygen containing gas in the presence of:
(a) a catalytic amount of a cobalt (II) compound,
(b) a primary aliphatic amine having the nitrogen atom attached to a tertiary carbon, and
(c) an alcohol selected from the group consisting of methyl alcohol, ethyl alcohol, isopropyl alcohol, butyl alcohol, 2,2,2-trifluoroethanol and benzyl alcohol,
wherein X is of the formula:

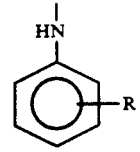

wherein R is individually selected from the group consisting of hydrogen, an alkyl having from about 1 to about 18 carbon atoms, an alkoxy having from about 1 to about 8 carbon atoms, a phenyl and an aralkyl having 7 to 12 carbon atoms.

2. The process of claim 1 wherein the cobalt (II) compound is a cobalt (II) salt selected from the group consisting of cobalt (II) naphthenate, cobalt (II) octoate, cobalt (II) laurate, cobalt (II) stearate, cobalt (II) linoleate, cobalt (II) acetylacetonate, cobalt (II) nitrate, cobalt (II) fluoride, cobalt (II) sulfate, cobalt (II) carbonyl, and cobalt (II) chloride.

3. The process of claim 1 wherein the primary amine is of the formula:

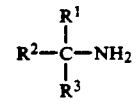

wherein $R^1$, $R^2$ and $R^3$ may be the same or different and are independently selected from the group of radicals consisting of an alkyl having 1 to 20 carbon atoms, or a hydroxy or alkoxy substituted alkyl having 1 to 16 carbon atoms and wherein the total number of carbon atoms for $R^1$, $R^2$ and $R^3$ does not exceed 20.

4. The process of claim 1 wherein R is independently selected from the group of radicals consisting of hydrogen and an alkyl having 5 carbon atoms.

5. The process of claim 1 wherein the alcohol is methyl alcohol.

6. The process of claim 1 wherein the cobalt compound is cobalt (II) chloride.

7. The process of claim 1 wherein the primary amine is t-butylamine, t-octylamine or 2-amino-2-methyl-1-propanol.

* * * * *